(12) United States Patent
Gibbons (10) Patent No.: US 8,460,163 B2
(45) Date of Patent: Jun. 11, 2013

(54) CALF ENHANCER FOR THE LOWER EXTREMITY

(76) Inventor: Vincent B Gibbons, Stone Mountain, GA (US)

( * ) Notice: Subject to any disclaimer, the term of this patent is extended or adjusted under 35 U.S.C. 154(b) by 777 days.

(21) Appl. No.: 12/583,047

(22) Filed: Aug. 13, 2009

(65) Prior Publication Data

US 2011/0040225 A1    Feb. 17, 2011

(51) Int. Cl.
*A63B 21/00*    (2006.01)
(52) U.S. Cl.
USPC .............................. 482/79; 482/80
(58) Field of Classification Search
USPC ...................................... 482/79, 80
See application file for complete search history.

(56) References Cited

U.S. PATENT DOCUMENTS

| | | | | |
|---|---|---|---|---|
| 5,035,421 A | * | 7/1991 | Scheller | 482/79 |
| 6,063,013 A | * | 5/2000 | Vathappallil | 482/121 |
| 6,935,991 B1 | * | 8/2005 | Mangino | 482/51 |

* cited by examiner

*Primary Examiner* — Jerome w Donnelly

(57) ABSTRACT

An ingenious calf, shin and ankle rehabilitation and exerciser apparatus for engagement with the lower leg muscles and ankle comprising of a rigid sole plate member having a sole plate protective pad and affixed fastening sole straps for securing foot to sole plate member, an attachable fulcrum heel ball member for attaching to the bottom of heel section. Sole plate member is pivotally attached to a rigid cross brace member which is comprised of a fastening shin straps affixed to a shin protective pad member to secure the lower leg to a rigid pivoting back support member that is pivotally engaged to cross brace member. Cross brace engages the toe section of sole plate member via an engaging biasing resistance means that provides posterior and anterior resistance not limited to isotonic and isometric for the flexing of the foot and ankle not limited to dorsi-flexion, plantar-flexion, inversion or eversion.

2 Claims, 7 Drawing Sheets

CALF ENHANCER FOR THE LOWER EXTREMITY

CROSS-REFERENCES TO RELATED APPLICATIONS

This application claims the benefits of U.S. Pat. No. 6,503,178, filed Aug. 15, 2008.

BACKGROUND OF THE INVENTION

1. Field of Invention

The concept of the "Calf Enhancer" is that of an exercise and rehabilitation device that is specifically designed to effectively isolate, tone, build or rehabilitate the anterior and posterior muscles of the lower extremity in a fashion which can be easily accomplished at home or where ever desired, without the need for weights or bulky stationary equipment.

2. Description of Prior Art

Studies have shown that muscles of the lower extremity, particularly the calf and shin muscles are not only among the hardest muscles to develop in the body but also among the most important as well as the most neglected. Although these muscles play a major part in our every day lives whether you are athletic or not, they are often taken for granted until injured. For example, if your calf muscles are too tight; they can't take sudden stress; as a result they strain or tear causing you real grief.

Injuries to the lower extremity are either tears of the juncture between the medial half of the calf muscle (the inner part, technically called the Gastrocnemius); Shin splints which is a painful condition that affects the Tibialis Anterior muscle of the shin and is often the result of weak shin muscles in relation to the calf muscles or a strain or rupture of the Achilles' tendon. In most cases, the aforementioned is caused by poor calf muscle flexibility due to the lack of stretching.

Injuries such as those describe above are very serious, especially those involving the Achilles tendon which more than often require surgery. These injuries can be prevented in a relatively easy fashion. You simply must keep the muscles of your lower extremity stretched, flexible and strengthen at all times with the aid of some type of calf machine or low impact workout that targets the areas in question.

Today's calf machines are bulky, weighty, stationary equipment designed for in-house use in the gyms and fitness centers only. They also require a considerable amount of weight to be somewhat effective.

Originally, in order to work the calf muscles you had to place a weight bar on your shoulders with the desired weight on each side and raise up on your toes either from a flat surface or place a board, preferably a 2.times.4 or any thing flat, stable and about three to five inches thick under the ball of your foot to allow a broader range of motion to work the calves some what effectively. The problem with this method is that not only do you have to focus on the exercise itself, but you have to focus on balancing the weight while you rise up on your toes which take away from the main focus, your calves.

Although this method is still widely used today, there have been several machines invented specifically for the calves. While the method of adding resistance is relatively different, the actual exercise and objective remains the same. There are two basic types of calf machines: the standing calf raise and the seated calf raise.

The standing calf raise is basically the same as using a straight bar on your shoulders with weights on either side but with out the worry of trying to balance the weight and lift at the same time. The standing calf machines regardless of the brand are very bulky and heavy machines, often weighing a minimum of 500 pounds and are very expensive. The standing calf machines are none portable and are designed specifically for the gyms and fitness centers which make them convenient only at the facilities that are housing them.

The deficiencies surrounding these machines are all the same: the standing calf raise, though relatively effective doesn't eliminate the tendency to bounce the weight when fatigue sits in which in terms is very ineffective in working the calves. In addition to bouncing, the standing calf machines allows you the option of bending the knees, and in essence promote cheating on the press; that's when you do not raise all the way up on your toes to fully contract the calf muscles or cheating on the decline; that's when you do not go down far enough to extend and or stretch the calf muscles and the Achilles' tendon which as a result is very ineffective in working the calves and can be the catalyst for future injuries. Although it is possible for you to work the calves individually, the standing calf machines are designed to work both of the calves simultaneously which makes it some what uncomfortable, and puts a bit of a strain on the lower back and spine when done individually. The seated calf machines though extremely different in design from the standing calf machines are very effective when used properly. They allow one to ingeniously be in a seated position while working the calves. Compared to the standing calf machines, the seated calf machines are relatively small, taking up half the space of the standing calf machines and weigh a lot less, around 50 to 70 pounds without weights. The cost though roughly half of that of the standing calf machines is still relatively expensive.

Though extremely more practicable than the standing calf machines, the seated calf machines are not designed to be portable thereby limiting the availability only to the facility housing the machine. Also the seated calf machines require external weights which take up more space and add to its impracticability.

Although this design eliminates the added stress put on the back and shoulders caused by the standing calf machines, they too failed to eliminate the tendency to bounce the weight when fatigue. While the seated calf machines succeeded in eliminating the option of bending the knees, they failed in eliminating the option to cheat on the press; that's when you do not raise all the way up on your toes to fully contract the calf muscles or cheating on the decline; that's when you do not go down far enough to extend or stretch the calf muscles and the Achilles' tendon which as a result is very ineffective in working the calves and also like the standing calf machines can be the catalyst for future injuries.

There is no doubt that the prior arts give the calves a relative good work out but a relatively good work out is not good enough. The key to developing the various muscles of the lower extremity not limited to the calf muscles is isolation; something that the prior arts failed to explore and adopt. The muscles of the lower extremity are designed to work as a team and as long as they are working together, you are more than likely to tire before the muscles of the lower extremity. To achieve the optimal results, one must essentially isolate the muscles of the lower extremity from working as a team therefore forcing them to work independently rather the dependently and as a result, the muscles are forced to work harder.

Lastly, as mentioned earlier, the Achilles' tendon and the muscles of the shin more so than the calves go relatively unnoticed until an injury occurs. Although the seated calf machine by default is capable of providing an adequate stretch of the Achilles tendon, neither prior art has the capability or functionality to strengthen, stretch or build muscle mass in the muscles surrounding the shin. In addition, the prior arts are very impracticable, inconvenient and are absent of any functionality as it pertains to rehabilitating an injury to the lower extremity for various reasons most of which are mentioned above.

BRIEF SUMMARY OF THE INVENTION

First and for most, the "Calf Enhancer" is designed specifically to effectively isolate, tone, and workout all the muscles of the lower extremity effectively in a fashion which can be easily accomplished at home or where ever desired, without the need for weights or bulky stationary equipment.

Accordingly, several objects and advantages of my invention are as follows: though the "Calf Enhancer" may be referred to as a rehabilitation device, it is designed to be very portable; able to be taken and administered virtually anywhere. The "Calf Enhancer" is very light weight, weighing roughly one to two in a half pounds; a featherweight compared to the prior arts. It's extremely storage friendly, taking up the space of a medium to large size shoebox. The "Calf Enhancer" is also very inexpensive, costing a fraction of the cost associated with the prior arts. The "Calf Enhancer" is designed to be universal; one size fits all. Unlike the prior arts, the "Calf Enhancer" by design can be used effectively as a strengthening and muscle building device, a rehabilitation device and can be locked in position to be used as a medical boot.

Once the "Calf Enhancer" is strapped on and the desired resistance is attached accordingly to affect the posterior or anterior of the lower extremity, the user is automatically forced to either stretch the calf muscles and Achilles tendon or the various muscles that encompasses the shin; something that is essential before beginning any exercise or workout. From the start or stretched position, the innovative fulcrum heel attachment provides the necessary leverage to allow the user to point his or her toes downward as if they were rising up on their toes on the standing calf machine or the seated calf machine but unlike the prior arts, no bouncing is involved. Even when fatigued, you only have three options; stretch it out, work it out or both.

Additionally, when the resistance is attached to the rear of the "Calf Enhancer," the user is automatically forced to stretch the various muscles of the shin. From the start or stretched position, the innovative fulcrum heel attachment provides the necessary leverage to allow the user to flex his or her foot upward, strengthening the muscles surrounding the shin. No prior arts have this functionality.

The "Calf Enhancer" uses weight resistance biasing means of different pounds per resistance to give the user the required none wavering resistance.

As mentioned, one of the biggest advantages of the "Calf Enhancer" is that unlike the standing and seated calf machines, the "Calf Enhancer" is innovatively designed to strengthen and build muscle mass in all the muscles of the lower extremity, frontal and posterior. Although the "Calf Enhancer" was designed to give one that added advantage to enhance the muscles of the lower extremity, just as important or even more so; it is also designed for rehabilitation purposes as well. The "Calf Enhancer" can be used to rehabilitate the calf muscle after a strain, to rehabilitate or strengthen the shin muscles to reduce the chances of getting shin splints, to rehabilitate the ankle after an ankle sprain or breakage, and most importantly to rehabilitate the Achilles' tendon after a strain or tear. Further objects and advantages of my invention will become apparent from a consideration of the drawings and ensuing description.

REFERENCE NUMERALS IN DRAWINGS 12 sole plate.
13 traction sole.
14 toe section.
16 heel section.
18 heel ball.
20 cross brace.
22 pivoting back support.
23 cross brace anchors.
24 cross brace anchor.
26 strap anchors.
28 adjusting pin holes.
30 sole plate anchors.
32 ankle pivot adjusting mechanism.
34 adjusting pivot holes.
36 shin protective pad.
35 insole.
37 insole padding.
38 sole plate rear anchor.
39 heel padding.
40 sole plate protective pad.
41 ankle pivot area.
44 transversely opposing slots.
46 pivoting support pad.
48 engaging biasing resistance means.
50 fastening shin straps.
52 fastening sole straps.

DETAILED DESCRIPTION OF THE INVENTION

Figure 1:
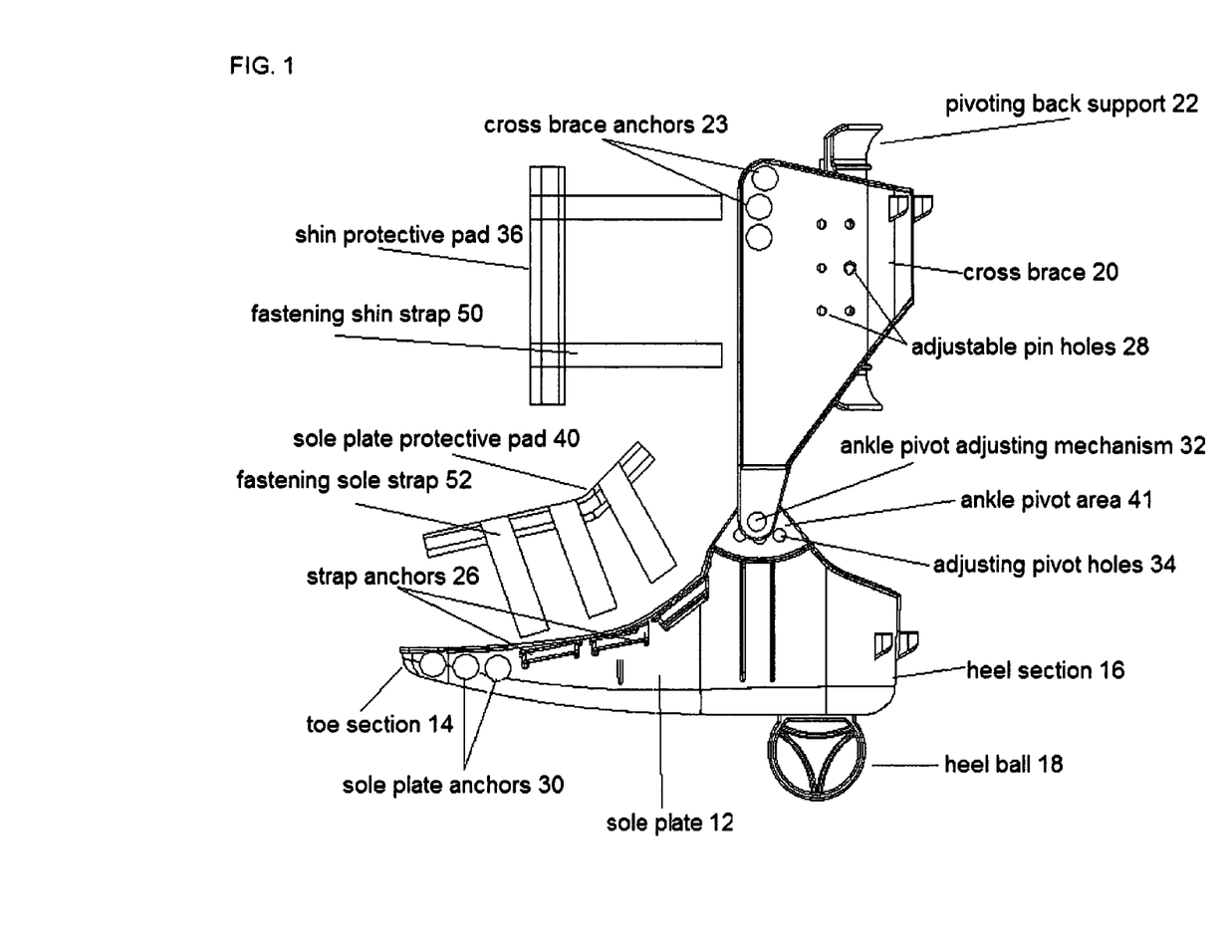
FIG. 1 is a detailed, perspective side view of the Calf Enhancer.
Figure 2:
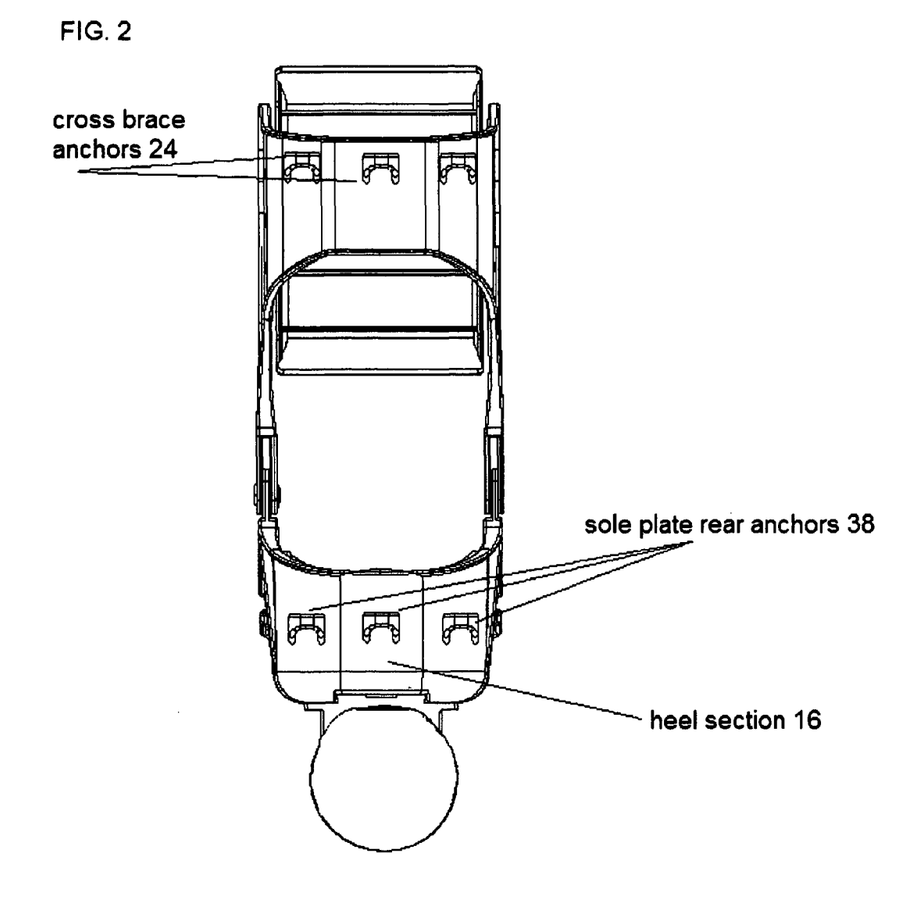
FIG. 2 is a detailed, perspective, rear view of the Calf Enhancer.
Figure 3:
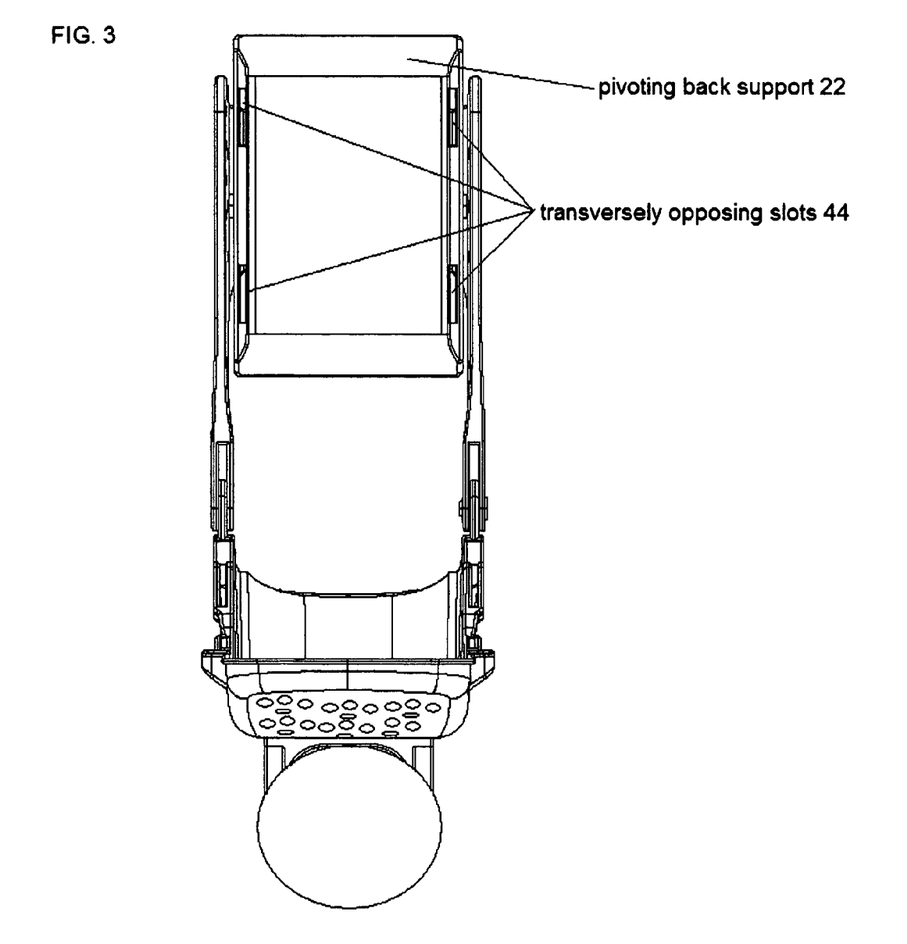
FIG. 3 is a perspective front view of the Calf Enhancer and the transversely opposing slots.
Figure 4:
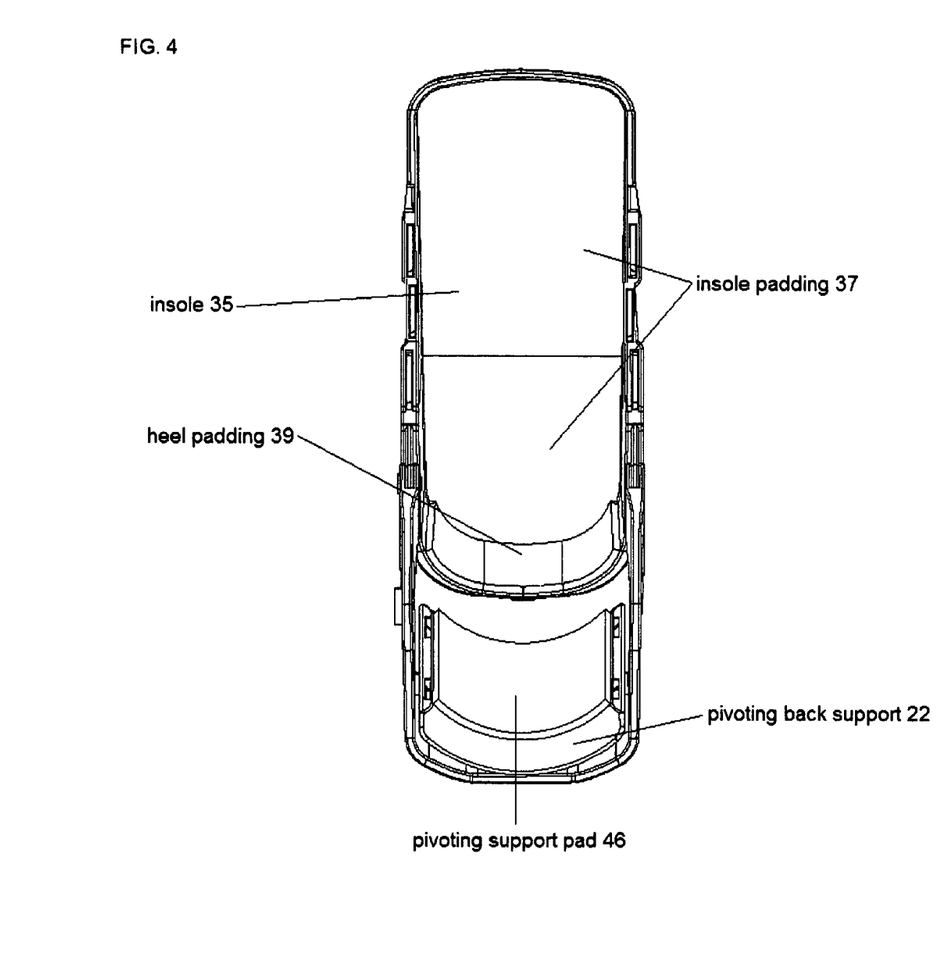
FIG. 4 is a detailed perspective top view of the insole pads, heel pad, and pivoting support pad.
Figure 5:
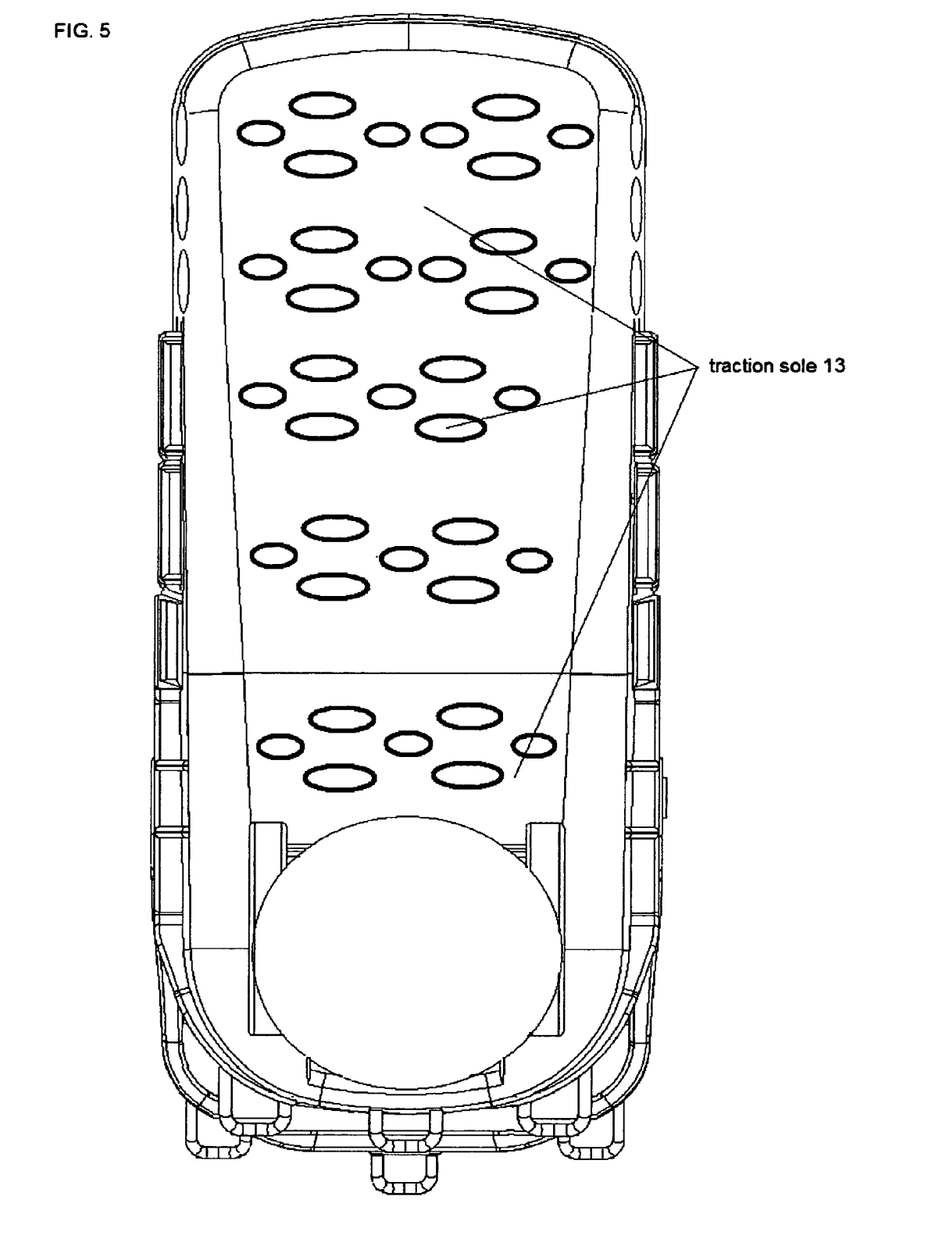
FIG. 5 is a detailed perspective bottom view of the rubber traction sole and fulcrum heel attachment.
Figure 6:
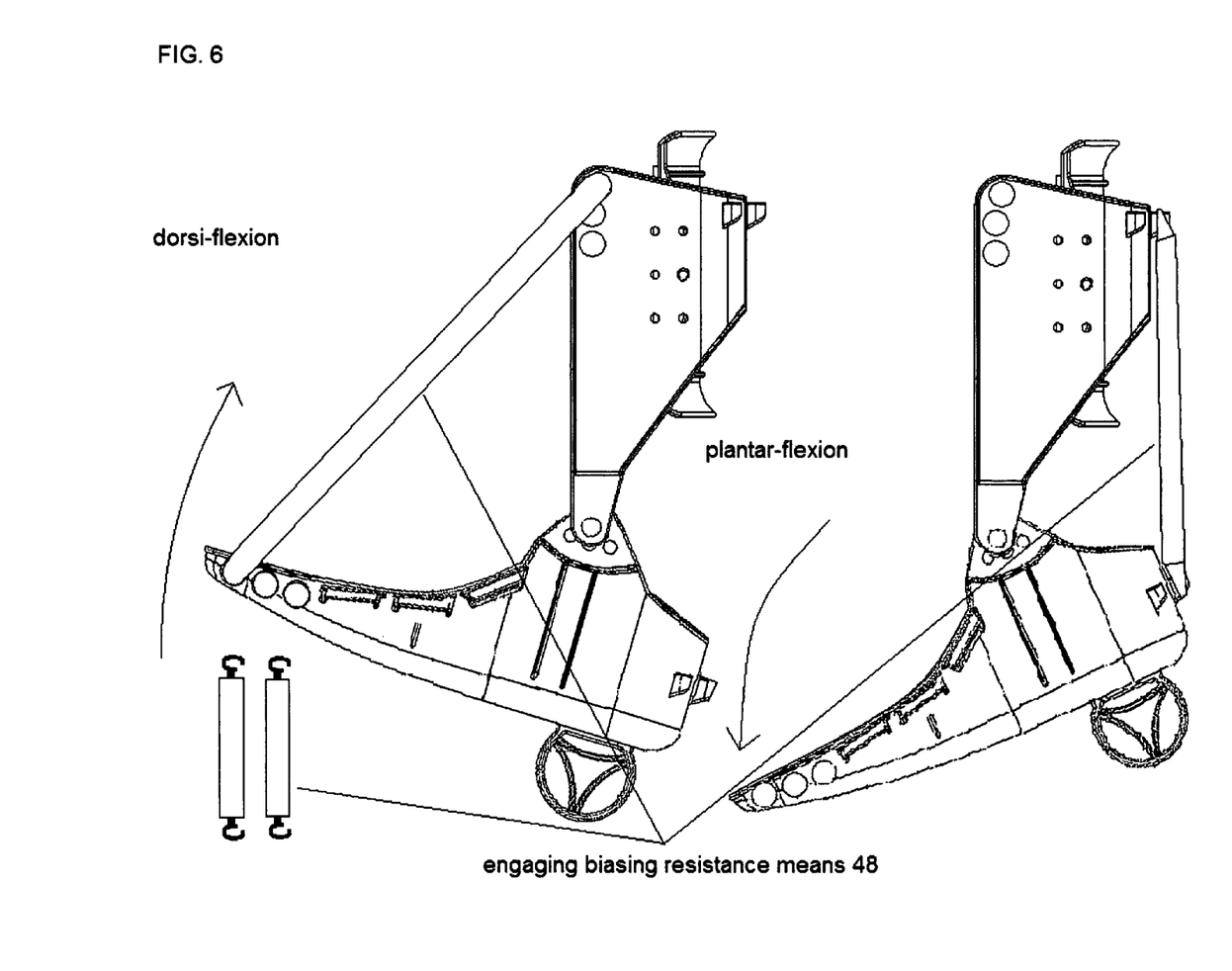
FIG. 6 is a perspective side view of the invention dorsi-flexion, plantar-flexion and attached engaging biasing resistance means.
Figure 7:
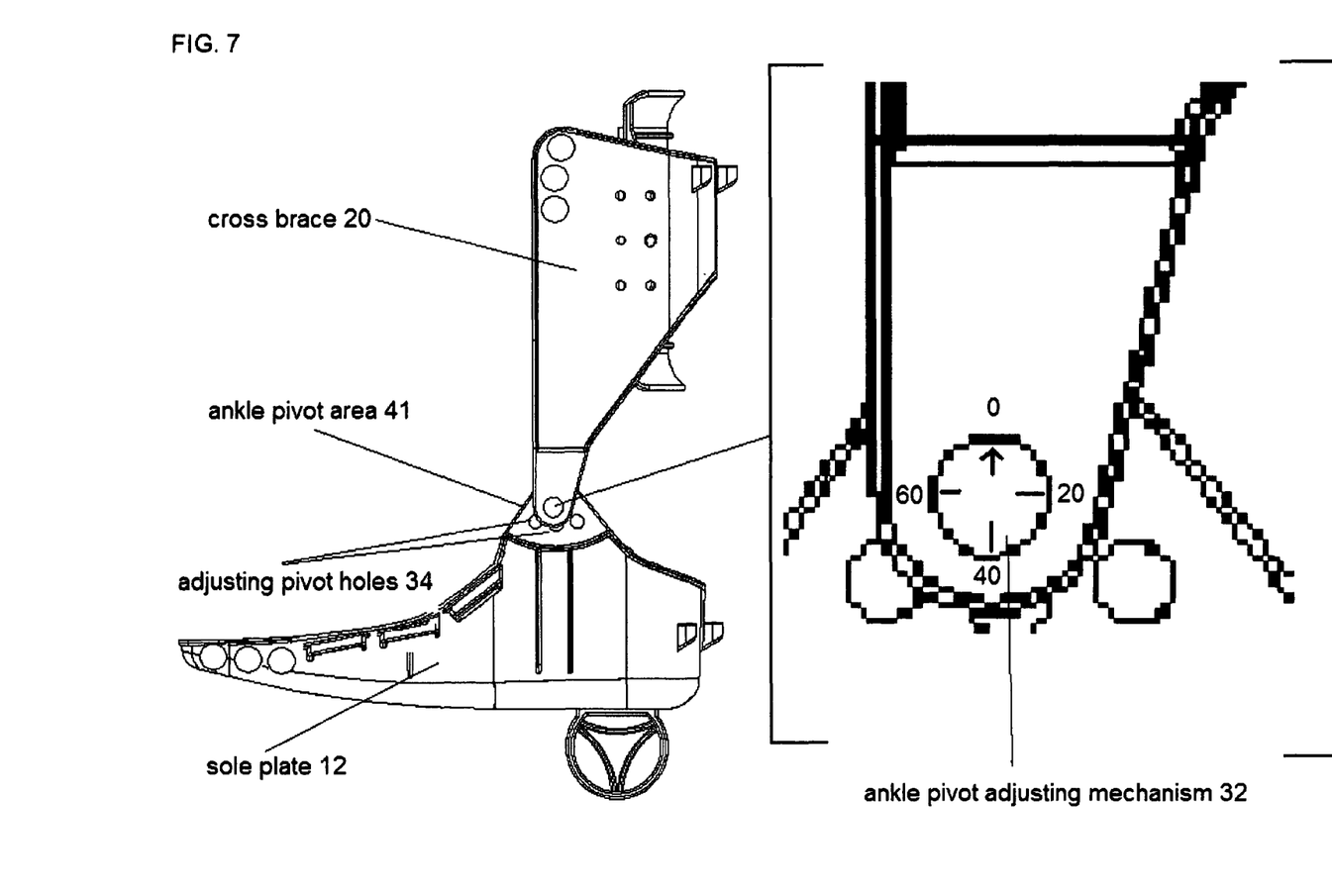
FIG. 7 is a perspective exploded view of the ankle pivot adjusting mechanism, ankle pivot area and adjusting pivot holes.

The embodiments of the present invention are described below. Be advised that the present invention is not limited to these embodiments, emphasis instead generally being placed upon illustrating the principles of the invention. FIG. 1 is a schematic representation of the invention and its principles which are explained as follows:

As shown in FIG. 1, a sole plate 12 of relative size and shape as to accommodate either foot wearing or not wearing a shoe is comprised of rigid material with a toe section 14 and a heel section 16. A plurality of sole plate anchors 30 positioned transversely on both sides of the toe section 14 to accommodate the ends of a engaging biasing resistance means 48 comprising the functionality of both isotonic and isometric resistance as shown in FIG. 6. A plurality of strap anchors 26 affixed diagonally extend outward on both sides of sole plate 12 as shown in FIG. 1, whereby a fastening sole straps 52 affixed to a sole plate protective pad 40 of predetermined size thickness and comfort loops through to fasten sole plate protective pad 40 to the top medial section of user foot providing adequate pressure to comfortably securing foot in place. As shown in FIGS. 1 and 7, a plurality of adjusting pivot hole 34 strategically placed within a ankle pivot area 41 positioned transversely on both sides of sole plate 12 to duplicate various ankle alignments and facilitate the natural movement of the ankle pivot adjusting mechanism 32 adjacently located and extending from a cross brace 20 which is comprised of a rigid material. As shown in FIG. 2, a plurality of sole plate rear anchors 38 extending outward and strategically affixed above the heel section 16 to anchor the ends of the engaging biasing resistance means 48 FIG. 6. As shown in FIG. 1, a detachable fulcrum heel ball 18 comprised of a rigid material and traction covered surface is attached beneath the heel section 16 providing ample leverage for maximum flexibility not limited to dorsi-flexion plantar-flexion inversion eversion inversion plantar-flexion and eversion dorsi-flexion. As shown in FIG. 5, a traction sole 13 comprised of a soft resilient robust material for traction and additional cushion while walking. As shown in FIG. 1, a pivoting back support 22 advocated by cross brace 20 pivotally comprised of a rigid material conforms to the various dimensions of the posterior area of user lower extremity. A plurality of cross brace anchors 23 positioned at the frontal summits of cross brace 20 to anchor the ends of the engaging biasing resistance means 48. A plurality of adjusting pin holes 28 allows the pivoting back support 22 to be adjusted horizontally and vertically for leverage or comfort. As shown in FIGS. 1 and 2, a cross brace anchors 24 affixed near the summit of the posterior area of cross brace 20 to accommodate the ends of the engaging biasing resistance means 48 FIG. 6. As shown in FIG. 1, a plurality of fastening shin straps 50 affixed to a shin protective pad 36 comprised of predetermined size thickness and comfort is looped through a plurality of transversely opposing slots 44 as shown in FIG. 3 and around pivoting back support 22 to secure user lower extremity snugly and comfortably against the pivoting back support 22. As shown in FIGS. 1 and 4, a insole padding 37 comprised of predetermined size thickness and comfort is affixed throughout a insole 35 of sole plate 12. A heel padding 39 comprised of predetermined size thickness and comfort is affixed to the inner wall of heel section 16. A pivoting support pad 46 comprised of predetermined size thickness and comfort is fixed to the anterior of pivoting back support for added support and comfort.

Operation of Invention—FIGS. 1, 2, 3, 4, 6, 7

The first use of the "Calf Enhancer" is consistent with that of a device designed to effectively strengthen, tone and build muscle mass in the calves and provide flexibility to the Achilles tendon and is administered as follows:

In use, the user would first attach the fulcrum heel ball 18 to its respective position underneath the heel section 16 of sole plate 12. Next, the user would simply place foot with or without a shoe appropriately in the sole plate 12, toe pointing away from the heel section 16. Before securing the foot in place, the user would make sure that the ankle pivot adjusting mechanism 32 is aligned with the natural pivot of the user's ankle to allow the sole plate 12 and the cross brace 20 to pivot simultaneously and naturally with the user's ankle and lower extremity. The user would then strap foot snugly by fastening the sole plate protective pad 40 to the top medial section of the foot by threading the fastening sole straps 52 through the strap anchors 26 positioned on both sides of sole plate 12. The user would apply enough pressure to tighten the fastening sole straps 52 to allow sole plate protective pad 40 to secure the heel and sole of the user foot firmly against the insole 35 and the interior wall of the heel section 16. The user would then fasten the fastening sole straps 52 accordingly to maintain the snug fit established. Next the user would raise the cross brace 20 up against the posterior or rear section of the lower extremity making sure to adjust the pivoting back support 22 so that it rest comfortably against the lower extremity with the top section resting just below the bottom of the calf muscle. Once the desired position of the pivoting back support 22 is obtained, the user would secure the support of cross brace 20 with the shin protective pad 36 by pulling and simultaneously looping the fastening shin straps 50 through the transversely apposing slots 44 positioned on both sides of the pivoting back support 22 and around the pivoting back support 22 applying enough pressure as to tighten and fasten comfortably the pivoting back support 22 to the lower extremity. Now that the "Calf Enhancer" is comfortably secured, the user would determine the desired resistance from a plurality of engaging biasing resistance means 48 choices. To install the engaging biasing resistance means, the user would begin by attaching the connecting end of one end of an engaging biasing resistance means 48 to one of the plurality of sole plate anchors 30 located within the toe section 14 on either side of sole plate 12. The user would then connect the other end of the same engaging biasing resistance means 48 indiscriminately to one of the plurality of cross brace anchors 23 located on the same side or opposite side near the frontal summit of cross brace 20 by pulling the toe section 14 of sole plate 12 upward toward the shin to allow for anchor engagement. To add more resistance the user has the option to add a plurality of additional engaging biasing resistance means 48 to both side of the "Calf Enhancer." Once installed, the engaging biasing resistance means 48 will instantly provide vertical resistance by pulling the front of the foot upwards towards the shin providing an optimal stretch to the Achilles tendon and the calf muscles. The user will then attempt to point the toe downward as if he or she was rising up on the toes doing a calf raise by which this action would counter the existing pulling action of the engaging biasing resistance means 48. The user will continue this process alternating between dorsi-flexion, raising the foot upwards and plantar-flexion, pointing the toe towards the ground. With the innovative fulcrum heel ball 18 attached, the various types of flexion that can be performed is only limited to the flexibility of the user's ankle. For maximum effectiveness the user would perform this maneuver adequately while in a seated position. The use of the "Calf Enhancer" in this manner is guaranteed to provide an extremely effective calf work out that would increase flexibility to the Achilles tendon and isolate the calf muscles in a manner that produce muscle tone and mass more effectively than that of conventional means.

The second use of the "Calf Enhancer" is consistent with that of a device designed to effectively strengthen, tone and build muscle mass in the shin which include but not limited to the Tibialis anterior muscle and the Soleus anterior muscle which are common areas associated with Shin Splints or pain associated with the muscles surrounding the Tibia. Although the cause of Shin Splints varies, one of the main causes is the lack of flexibility and strength in the Tibialis and Soleus muscles as well as the ankle joint itself. The "Calf Enhancer" is perfectly designed to effectively strengthen and establish flexibility in the areas in question and is accomplished as follows:

The user would strap on the "Calf Enhancer" as was done in the first usage above. Once the "Calf Enhancer" is snugly fastened, instead of connecting one end of the engaging biasing resistance means 48 to one of the plurality of sole plate anchors 30 of sole plate 12 and the other end to one of the plurality of cross brace anchors 23 of cross brace 20 as was done above, the user would connect one end of an engaging biasing resistance means 48 to one of the plurality of sole plate rear anchors 38 positioned above the heel section 16 of sole plate 12. Next the user will point the toe downward to facilitate connection of the second end of the same engaging biasing resistance means 48 aforementioned to one of the plurality of cross brace anchors 24 positioned near the summit of the posterior area of the cross brace 20. The established connection of the engaging biasing resistance means 48 instantly provides a substantial stretch to the various muscles of the shin. Next the user will counter the existing resistance by flexing the toe upwards toward the shin which is often referred to as dorsi-flexion. As mentioned in the first usage, for maximum effectiveness the user would repeat this maneuver adequately while in a seated position. The use of the "Calf Enhancer" in this manner is guaranteed to provide an extremely effective stretch as well as increase strength, tone and build muscle mass in the target area.

The third and probably the most innovative use of the "Calf Enhancer" is consistent with that of an advanced medical boot for rehabilitation purposes. After an immobilizing injury not limited to a broken or severe ankle sprain, torn or strained Achilles tendon or any injury that would require the immobilization of the lower extremity for an extended amount of time, the "Calf Enhancer" can be easily converted to an advanced medical boot to allow for a swift recovery. The conversion and advantages of the "Calf Enhancer" as an advance medical boot is as follows:

Before strapping on and fastening the "Calf Enhancer" snugly in place as was done in the previous usage, the user must first make sure that the fulcrum heel ball 18 is detached. Secondly the user must adjust the ankle pivot adjusting mechanism 32 of the cross brace 20 to its locking position, locking the cross brace 20 and sole plate 12 at a 90 degree angle. Once this is done, the user can strap on and fasten the "Calf Enhancer" to the lower extremity as was done in the previous practices. Once strapped on, the "Calf Enhancer" will keep the ankle and foot immobilized. The soft padding of insole padding 37, heel padding 39, shin protecting pad 36 and sole plate protecting pad 40 will provide ample cushioning. Additional cushion can be added if needed. In addition to the various cushioning aforementioned, the traction sole 13 of sole plate 12 will provide additional cushion and ample traction while walking. Once the user starts to gain some degree of mobility, upon the recommendation of a physician, the ankle pivot adjusting mechanism 32 of cross brace 20 can be adjusted accordingly to minor the user's degree of mobility. As the user's mobility nears the natural limits of normal mobility, the "Calf Enhancer" is capable of allowing a lesser resistance means than the engaging biasing resistance means 48 to be connected to the sole plate anchors 30 of sole plate 12 and the cross brace anchors 23 of cross brace 20 to provide a measured degree of resistance while walking. This process will considerably lesson the time it takes to rehabilitate the lower extremity over conventional means with the added benefit that the user can perform all the usages explicitly covered or implicitly implied virtually any where.

Accordingly, the reader will see that the "Calf Enhancer" of the invention provides a highly reliable, lightweight, yet effective device that can be used by persons of almost any age any where. In addition, the reader will also see that the "Calf Enhancer" of the invention is more that just a device used to build muscle mass, tone and effectively stretch all the muscles of the lower extremity including the Achilles' tendon, but a device that is ingeniously designed for rehabilitation purposes as well. Further more, the "Calf Enhancer" has the additional advantages in that:

It is extremely safe.

It can be used in bed or in a wheelchair.

It can be worn with or with out shoes.

The structure of the invention permits the patient easy entrance to and exit from the device.

Asset for any sport: Basketball, Football, Baseball, Tennis, Volleyball, Soccer, Track and Field, Gymnastics, Cheerleading, Hockey, Boxer, Ballet, Swimmers, Skiers etc.

While the above descriptions explain the three major specificities of use, these should not be construed as limitations on the scope of the invention, but rather as an exemplification of one preferred embodiment thereof.

Accordingly, the scope of the invention should be determined not by the embodiments illustrated, but by the appended claims and their legal equivalents.

The invention claimed is:

1. A toning, strengthening and rehabilitation apparatus for the lower extremity comprising:
    a rigid sole plate member having a heel and toe portion of sufficient size to accommodate various sizes of the human foot;
    said sole plate member having a plurality of anterior and posterior anchors strategically affixed for engaging a plurality of biasing resistance means;
    said sole plate member having a resilient, cushioning and traction sole means affixed throughout the underside;
    said sole plate member having an engaging means whereby a fulcrum member is optionally attached proximally beneath said sole plate member;
    said sole plate member having a pivot area, upward extending on opposite sides of said sole plate member terminating proximally before;
    engaging elongated members of a cross brace support member wherein said cross brace support member is comprised of a rigid material;
    said sole plate member having an adjustable means affixed laterally whereby said adjustable means dictates dorsi-flexion and plantar-flexion; and
    said cross brace support member having a medial pivot back support member and a plurality of anchors for engaging a plurality of said biasing resistance means.

2. A toning, strengthening and rehabilitation apparatus of claim 1, wherein said engaging biasing resistance means exert sustained resistance not limited to isotonic or isometric resistance.

* * * * *